United States Patent
Geist et al.

(10) Patent No.: US 8,361,102 B2
(45) Date of Patent: Jan. 29, 2013

(54) K-WIRE AND METHOD FOR SURGICAL PROCEDURES

(75) Inventors: Wyatt Drake Geist, Davie, FL (US); Arden Allen Geist, Sr., Indiatlantic, FL (US)

(73) Assignee: Safe Wire Holding, LLC, Davie, FL (US)

( * ) Notice: Subject to any disclaimer, the term of this patent is extended or adjusted under 35 U.S.C. 154(b) by 259 days.

(21) Appl. No.: 12/823,791

(22) Filed: Jun. 25, 2010

(65) Prior Publication Data

US 2010/0331893 A1 Dec. 30, 2010

Related U.S. Application Data

(60) Provisional application No. 61/220,828, filed on Jun. 26, 2009.

(51) Int. Cl.
*A61M 29/00* (2006.01)
(52) U.S. Cl. ..................................................... 606/198
(58) Field of Classification Search ............. 604/164.01, 604/104, 106, 107; 606/313, 326–327, 198; 600/200, 434, 585, 567
See application file for complete search history.

(56) References Cited

U.S. PATENT DOCUMENTS

| | | | |
|---|---|---|---|
| 4,654,028 | A | 3/1987 | Suma |
| 5,217,484 | A | 6/1993 | Marks |
| 5,431,651 | A | 7/1995 | Goble |
| 5,433,723 | A | 7/1995 | Lindenberg et al. |
| 5,509,919 | A | 4/1996 | Young |
| 5,653,716 | A | 8/1997 | Malo et al. |
| 5,795,308 | A | 8/1998 | Russin |
| 7,169,160 | B1 | 1/2007 | Middleman et al. |
| 7,367,975 | B2 | 5/2008 | Malecki |
| 7,575,578 | B2 | 8/2009 | Wetzler et al. |
| 7,914,493 | B2 | 3/2011 | Venbrux et al. |
| 2005/0267555 | A1 | 12/2005 | Marnfeldt et al. |
| 2006/0064101 | A1 | 3/2006 | Arramon |
| 2007/0191778 | A1* | 8/2007 | Venbrux et al. .......... 604/164.13 |
| 2007/0239159 | A1 | 10/2007 | Altarac et al. |
| 2007/0270896 | A1 | 11/2007 | Perez-Cruet |
| 2008/0071223 | A1 | 3/2008 | Stauber |
| 2009/0182245 | A1 | 7/2009 | Zambelli |
| 2009/0275946 | A1 | 11/2009 | Duncan |

* cited by examiner

*Primary Examiner* — Sameh Boles
(74) *Attorney, Agent, or Firm* — McHale & Slavin, P.A.

(57) ABSTRACT

A surgical guide wire or K-wire and method of use are provided. The K-wire or guide wire has opposite end portions and a shank portion in between. One end portion has a deformable end portion that, once outside of a confining guide passage, can be deformed to present a projected forward facing area that is larger than the transverse cross section of the K-wire or guide wire while in the passage. The increased area will provide increased resistance to additional forward axial movement into the surgical site.

16 Claims, 4 Drawing Sheets

K-WIRE AND METHOD FOR SURGICAL PROCEDURES

CROSS REFERENCE TO RELATED APPLICATION

This application claims the benefit under 35 U.S.C. 119(e) of U.S. Provisional Patent Application No. 61/220,828, filed Jun. 26, 2009, entitled, "K-WIRE AND METHOD FOR SURGICAL PROCEDURES", the entirety of which is incorporated herein by reference.

FIELD OF INVENTION

The present invention relates to an improved guide wire or K-wire for use in surgical procedures such as orthopedic procedures and in particular, spinal procedures such as percutaneous pedicle screw constructs.

BACKGROUND OF THE INVENTION

In certain surgical procedures, a K-wire (Kirschner wire) or guide wire is used in combination with a surgical tool such as a jamshidi needle. The jamshidi needle is used to form a hole through bone as a first step in certain medical procedures like attaching a screw to a pedicle. The K-wire or guide wire is inserted through the needle into the interior of the bone, which if not done properly can injure the patient, particularly if it engages certain sensitive parts which may include breaching the anterior cortex of a vertebral body. The K-wire or guide wire is used as a portal for certain surgical steps like guiding a tap, screw or screwdriver to the surgical site. The procedures oftentimes require the use of force which can cause a properly positioned K-wire or guide wire to move forward into the surgical site, which if excessive can move into contact where contact is to be avoided.

A K-wire or guide wire is generally cylindrical and has a diameter of about 3 millimeters, making it easy to move during use; in fact, the K-wire or guide wire is designed to move during its installation, but once installed its movement is not impeded, requiring care in its use. The cross sectional size of the K-wire though is limited by the tools and devices it is used with. Each tool or device is provided with a through bore for receiving the K-wire or guide wire, limiting the size and type of wire that can be used. Additionally, the K-wire is typically removed by passing through a through bore in a device or tool. Thus, to date, only K-wires with a small diameter, generally cylindrical round cross section, have been used which presents the problem in their use. It should also be noted that while the K-wires or guide wires illustrated herein include a solid center core, the K-wire or guide wire may be a hollow tubular member without departing from the scope of the invention.

The present invention provides a solution to this problem by providing an improved K-wire or guide wire which, when inserted, provides increased resistance to forward axial movement while still being usable with traditional surgical tools and devices.

DESCRIPTION OF THE PRIOR ART

U.S. Pat. No. 5,431,651 discloses a cross pin and set screw femoral and tibial fixation device for mounting a ligament graft. The device includes a drill guide for drilling a transverse hole. The drill guide is releasable from a first twist drill so as to leave it in place. The first twist drill is used to guide further drilling and passage of a fastener device. A K-wire or the first twist drill is used for guiding a second twist drill for enlarging the transverse hole and for guiding and turning a cannulated fastener device into a femoral bone end of the ligament graft. There is no feature on the K-wire to limit the extent of its insertion subsequent to it passing through the bone.

U.S. Pat. No. 7,575,578 discloses a surgical drill guide including a handle and an arm having an end which contacts a bone. The handle includes a plurality of slots or channels which receive a sleeve. The sleeve is used to guide a K-wire into the bone. The K-wire serves as a guide for drilling a tunnel into the bone. The K-wire does not include a feature to limit the extent of its insertion subsequent to it passing through the bone.

U.S. Published Patent Application No. 2007/0239159 discloses devices and system for placing bone stabilization components in an individual. In particular, the bone stabilization components are placed on the spine. Various tools, including a K-wire, are employed to properly locate, place and secure the devices in an individual.

U.S. Published Patent Application No. 2007/0270896 discloses a device for accessing the pedicle of a vertebra including a Jamshidi needle.

SUMMARY

The present invention involves the provision of a K-wire which can be used with traditional surgical tools and devices. The inventive guide wire or K-wire has an end portion that, upon exit from the through bore of a surgical tool or device, can be changed in a controlled manner to present a deformable end portion that will provide a forward face with a larger projected area than the end surface of the K-wire while in the through bore. The deformation may be induced mechanically from internal stress, thermally or otherwise.

The present invention also involves the provision of a method of conducting surgery utilizing a guide wire or K-wire. The method includes passing a guide wire or K-wire through a tool or device into a surgical slit with the guide wire or K-wire presenting a forward facing area of a first size. The guide wire or K-wire then has an end portion moved out of the tool or device where the forward end portion can be expanded to present a forward facing area of a second size larger than the first size. After use, the guide wire or K-wire may be extracted from the surgical site through a surgical tool or device.

BRIEF DESCRIPTION OF THE DRAWINGS

Like numbers used throughout the Figures designate like or similar parts and/or construction.

DETAILED DESCRIPTION OF THE INVENTION

Figure 1:
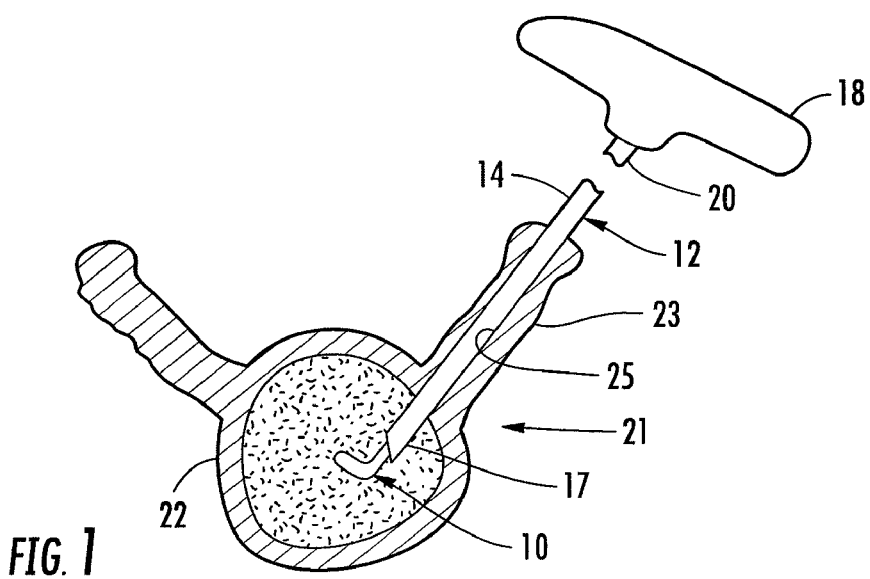
FIG. 1 is schematic plan view of vertebra showing a jamshidi needle extending through a pedicle.

While the present invention is susceptible of embodiment in various forms, there is shown in the drawings and will hereinafter be described presently preferred embodiments with the understanding that the present disclosure is to be considered an exemplification of the invention and is not intended to limit the invention to the specific embodiments illustrated.

Referring generally to the Figs., the reference numeral 10 designates generally a K-wire or guide wire usable in surgical procedures in combination with a surgical tool such as a Jamshidi needle 12, drill or tap (not shown), or a surgical device such as a screw, plate or implant. K-wires (also called Kirschner wires) or guide wires are well known in the art. Jamshidi needles are also well known in the art and have a shank 14 with a through bore 16 (as would a drill, tap or screw) and a sharpened distal end 17. A handle 18 may also be provided at the proximal end 20 of the shank 14 for facilitating insertion of the shank into a surgical site 21, such as a vertebra 22 with a pedicle 23 in a patient such as a human. A surgeon may manipulate the jamshidi needle 12 using the handle 18, and may also apply impact force to the shank 14 by striking the handle with a hand or impact tool such as a hammer. Jamshidi needles are used to penetrate bone in the performance of a surgical procedure such as attaching a screw 24 to bone. A rod not shown) may be installed in the through bore 16 during hole formation to increase rigidity of the shank 14. The rod is removed to provide a through bore 16 for the K-wire 10 insertion. After forming a hole 25 with the jamshidi needle 12, the K-wire or guide wire 10 is inserted into the interior of the bone and the jamshidi needle is removed, leaving the K-wire or guide wire in place. In some surgical procedures, like spinal surgery, the K-wire or guide wire is inserted through one wall of a bone, e.g., a pedicle 23 and is placed against an opposite bone wall. If care is not taken during surgery, the K-wire or guide wire may be pushed through the opposing bone wall creating a risk of injury. The present invention is a solution to this potential problem.

The K-wire or guide wire 10 is typically used as a pilot or guide for other surgical tools or devices such as drills, taps, plates, implants and screws. In the attachment of a screw 24 (FIG. 5B), the screw can have a through bore 44 that receives the K-wire or guide wire for guiding the screw to a drilled and tapped hole 25. After installation of the screw 24, the K-wire or guide wire 10 is then extracted through the through bore 27 of the screw 24 by simply pulling on the K-wire or guide wire to reduce the frontal area of the K-wire or guide wire substantially to its original size.

The K-wire or guide wire 10 has opposite end portions 26, 28 and a generally cylindrical intermediate portion 30 positioned between the end portions. The length of the K-wire or guide wire 10 is preferably long enough to extend beyond both ends of the surgical tool being used, e.g., a jamshidi needle 12. The K-wire or guide wire 10 is sized and shaped to be freely movable along the through bore 16. The end portion 28 will be referred to as the manipulative end and the end portion will be referred to as the operative end for convenience. Preferably, the entire length of the manipulative end portion 28 and the intermediate portion 30 is generally cylindrical to facilitate removal of a tool or device from an installed K-wire or guide wire 10.

The operative end portion 26 is provided with a section 32 that is controllably deformable. The section 32 may be an integral portion of the K-wire or guide wire 10 or attached thereto. Several different sections 32 are described below. In general, the section 32 is configurable to fit within the through bore 16 and freely movable therein. It is insertable into the through bore 16 for insertion into the surgical site 21 for use and for removal from a through bore in the tool or device. The K-wire or guide wire may also be removed prior to a later surgical step if it is no longer needed. For example, if the K-wire or guide wire is not needed to guide the screw 24 for insertion, it may be removed prior to attaching the screw 24. When outside of the through bore 16, the operative end 26 expands automatically or can be manually expanded to present an expanded face with a projected area greater than the transverse cross sectional area of the K-wire or guide wire 10 while positioned in the through bore 16. By way of example, the operative end 26 seen in FIG. 3 has a projected area of approximately (given that the end 33 of the bend at the intermediate section 30 of K-wire or guide wire 10 is rounded reducing the area slightly) L times W whereas the K-wire guide wire has a cross sectional area of $A=\pi r^2$ where r is equal to W/2. It is preferred that the reconfigured cross sectional projected area be at least about 1.5 times, and preferably at least about twice the size of the first cross sectional area of the K-wire or guide wire as described below.

Figure 2A:
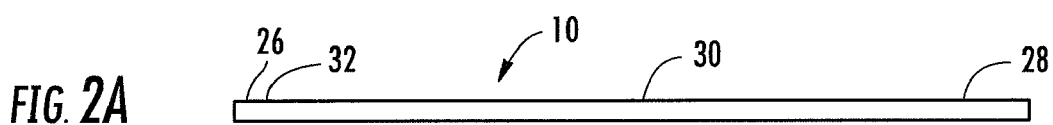
FIGS. 2A, 2B are side elevation views of a K-wire or guide wire showing two configurations of one end portion of the K-wire or guide wire.
Figure 2B:
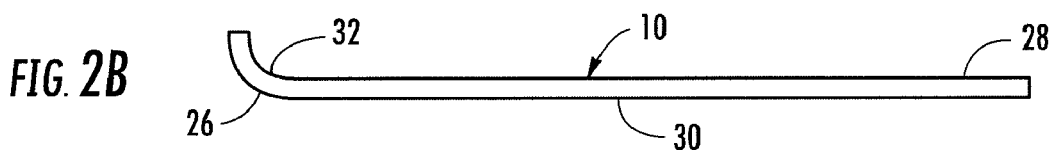
Figure 5A:
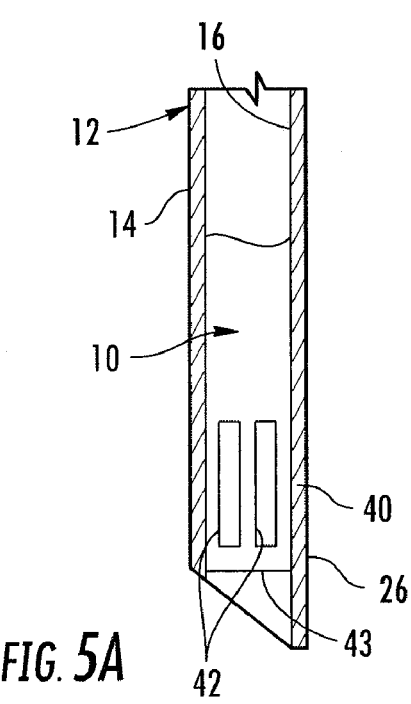
FIGS. 5A and 5B are enlarged fragmentary side views of an end portion of a K-wire or guide wire with one embodiment of reformable end portion.
Figure 5B:
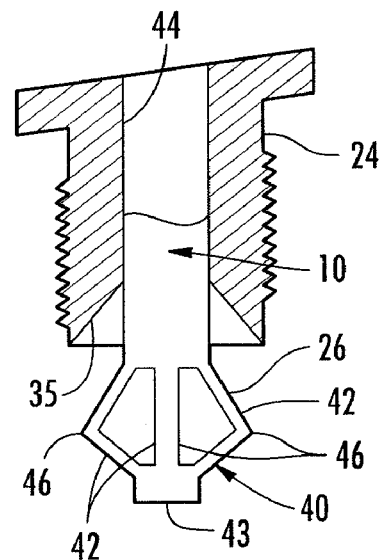

The K-wire or guide wire 10 or the deformable portion of the K-wire or guide wire may be made of a deformable material which will allow at least the operative end 26 to be configured between first and second configurations (see FIGS. 2A and 2B) with one configuration (FIG. 2B) presenting a larger projected area than the first (FIG. 2A) as discussed above. One suitable reconfigurable material is referred to as a shape memory alloy such as Nitinol. A reversible, solid phase transformation known as martensitic transformation is the force behind shape memory alloys. Such alloys are well known and form a crystal structure, which is capable of undergoing a change from one form of crystal structure to another. Temperature change and/or loading can initiate the shape transformation. By way of example, above its transformation temperature, Nitinol is superelastic, able to withstand deformation when a load is applied and return to its original shape when the load is removed. Below its transformation temperature, it displays the shape memory effect. When it is deformed below its transformation temperature, it will remain in that shape until heated above its transformation temperature, at which time it will return to its original shape. The original shape would then be the bent form and then it can be reformed cold to straight. Upon heating, the bend will return. The heat (or temperature increase) can be provided by contact with the patient. Elastically deformable materials may also be used, such as spring steel with high yield strength where stress is induced to change a shape is elastically released to change the shape of the deformed member back to its non stressed shape. An embodiment of the invention is shown in FIGS. 5A and 5B that could be made using a spring material and is described below. Plastically deformable materials might also be used for some operative end portion 26 configurations. The terms resiliently deformable, plastically deformable and spring are used generally to indicate a material property when the material is deformed during typical use of the K-wire or guide wire as described herein. Controlled bending can be induced by using controlled weak points such as a groove or the like at selected strategic locations. The embodiment in FIGS. 5A and 5B might also be used with a plastically deformable material. The screw 24 or other tool or device that is anticipated to be the last one used with the K-wire or guide wire 10 may be provided with a forcing cone 35 to help reconfigure the end portion 26 back to its unexpanded shape to conform it to fit within a passage like passages 16, 44 for insertion or removal. An embodiment of this form is seen in FIGS. 5A and 5B and is described below.

Figure 3:
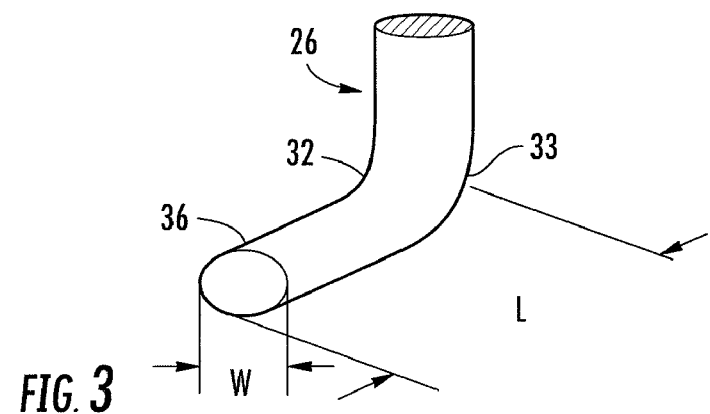
FIG. 3 is an enlarged fragmentary view of a K-wire or guide wire showing an end portion shown configured to present an expanded forward face.

In the embodiment shown in FIGS. 1-3, the operative end 26 has a laterally extending portion 36 when out of the through bore 16. The deformation to lateral extension may be provided as described above by applying heat to effect bending from memory. The portion 36 may be provided as a permanent bend in the K-wire or guide wire 10 which can then be deformed to straight by confinement in the through bore 16, and upon exit from the through bore will reassume its bent configuration. The material properties of the end portion 26 may be selected to provide for straightening of the bend for removal through a passage or bore which may be facilitated, e.g., by the use of a forcing cone 35. The lateral extension presents a larger projected area to further limit forward axial motion into the surgical site.

Figure 4:
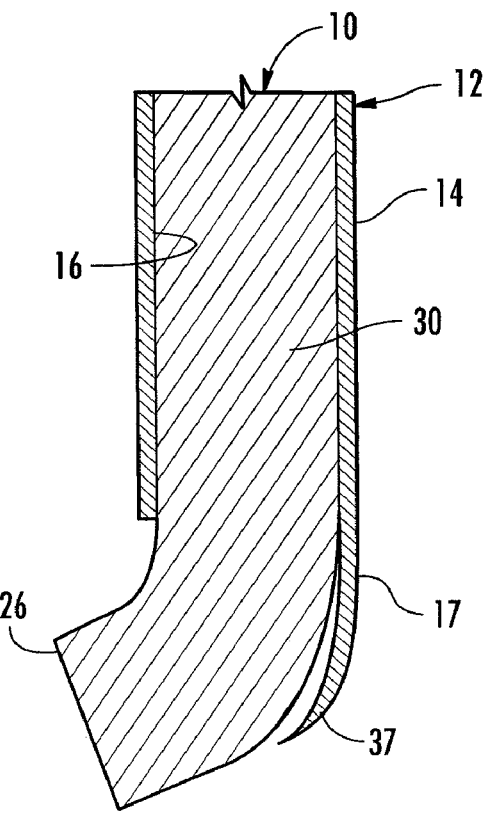
FIG. 4 is a fragmentary side sectional view of a jamshidi needle with a K-wire or guide wire in a through bore.

FIG. 4 shows a surgical tool configuration that can be used to facilitate directing a K-wire or guide wire 10 out of the through bore 16. It uses a curved tip 37 to direct the exiting K-wire or guide wire 10.

In the embodiment shown in FIGS. 5A and 5B, the operative end 26 is in the form of an expandable cage 40 having a plurality of rods 42 that can assume an extended position; FIG. 5A illustrates a contracted configuration of cage 40 when in a through bore 16 of shank 14. FIG. 5B illustrates the cage 40 in its expanded configuration and a screw positioned on the K-wire or guide wire 10. The embodiment of FIGS. 5A and 5B may be constructed in at least two ways, resiliently deformable rods 42 or plastically deformable rods 42. A memory metal alloy may be used. A polymeric material such as PEEK may also be used for at least the rods 42. If the rods 42 are elastically deformable, they can be formed as biased to an outward or expanded configuration, where once outside of the through bore 16 they will move outwardly to relieve induced stress to provide the expanded configuration like in FIG. 5B. The rods 42 may also be plastically deformable, and upon application of axial force will move to an expanded position as in FIG. 5B. When the K-wire or guide wire is in the through bore 16, the rods 42 assume or are in the collapsed configuration and when the rods 42 are outside of the bore, they assume or are forced into the expanded position providing an increased projected area for engagement with material in the surgical site as discussed above. It is to be noted that the rods may also be made of a memory alloy as described above. The forcing cone 35 may be used to facilitate removal of the K-wire or guide wire 10 through the through bore 44. The distal ends of the rods 42 may be held in place with an end cap 43. The projected area of the end portion 26 when expanded as seen in FIG. 5B would be that area defined or bounded by outermost extending portions of the rods 42 as at portions 46.

Figure 6B:
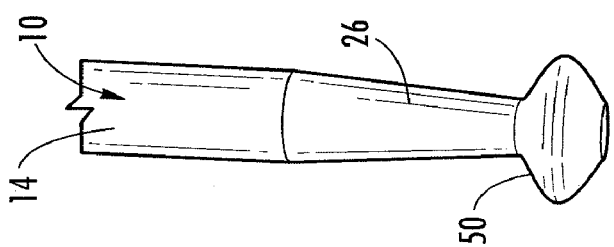
FIGS. 6A and 6B are enlarged side views of an end portion, expanded and unexpanded, of a further embodiment of a K-wire or guide wire of the present invention.
Figure 6A:
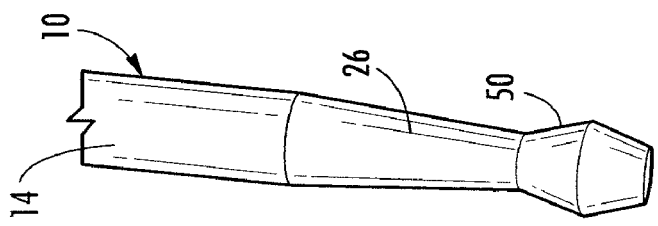

FIGS. 6A and 6B illustrate another embodiment of the invention. FIG. 6A shows an end portion 26 with an expandable end bulb 50 that may be made out of a memory alloy, that upon heating assumes the expanded configuration illustrated in FIG. 6B. This embodiment is particularly adapted for use when extraction of the K-wire or guide wire is other than through a tool or device passage.

Figure 7:
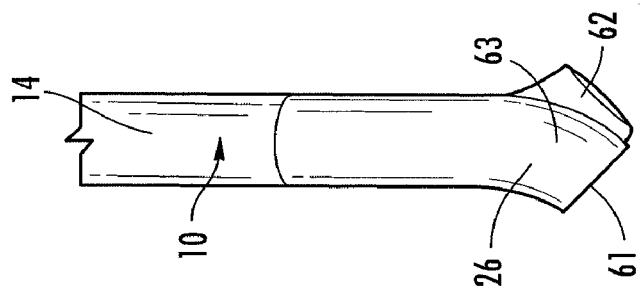
FIG. 7 is an enlarged side view of an end portion of a still further embodiment of a K-wire or guide wire of the present invention.

FIG. 7 illustrates another embodiment of the invention. It utilizes a pair of opposed legs 61, 62. The legs 61, 62 are constructed to move in an outward direction either from spring action or from otherwise reassuming a formed shape as from a temperature change as by using a memory alloy as described above. In the illustrated embodiment, the legs 61, 62 have overlying portions at 63.

Figure 8:
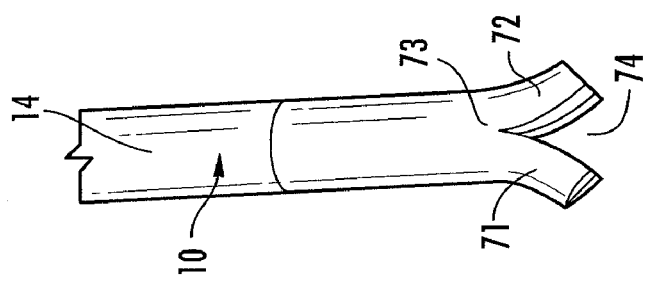
FIG. 8 is an enlarged side view of an end portion of a still further embodiment of a K-wire or guide wire of an end portion of the present invention.

FIG. 8 illustrates an additional embodiment of the invention and is similar to the form shown in FIG. 7 by having two legs 71, 72, but the legs do not overlap; but rather the legs diverge from a common area 73 and have a gap 74 therebetween when in the extended position as shown.

The embodiments of the invention shown in FIGS. 6-8 all utilize a shank 14 of one material and an end portion of another material such as a spring material or a memory alloy.

Figure 9:
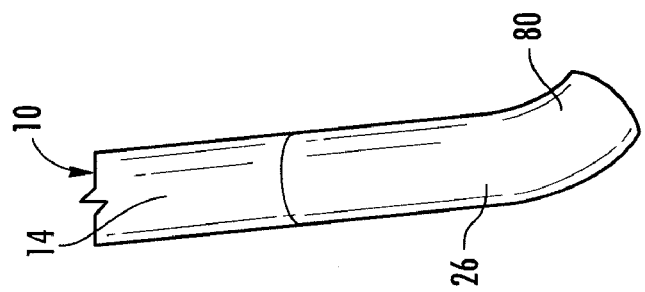
FIG. 9 is an enlarged side view of an end portion of an embodiment of the invention similar to that shown in FIG. 2B.

FIG. 9 illustrates a still further embodiment of the present invention. It is similar to the K-wire or guide wire 10 shown in FIG. 2 and has a shank 14 with an attached end portion 26 having a single extending leg 80 shown in its extended configuration. The portion 80 may be provided as a permanent bend in the K-wire or guide wire 10 which can then be deformed to straight by confinement in the through bore 16, and upon exit from the passage will reassume its bent configuration. The material properties of the end portion 80 may be selected to provide for straightening of the bend for removal through a passage which may be facilitated, e.g., by the use of a forcing cone. The lateral extension presents a larger projected area to further limit forward axial motion into the surgical site.

Figure 10:
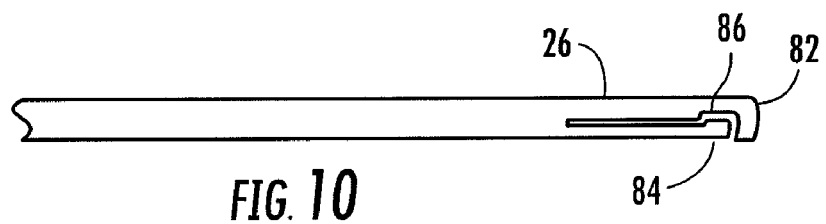
FIG. 10 is an enlarged side view of an end portion of a still further embodiment of the present invention.
Figure 11:
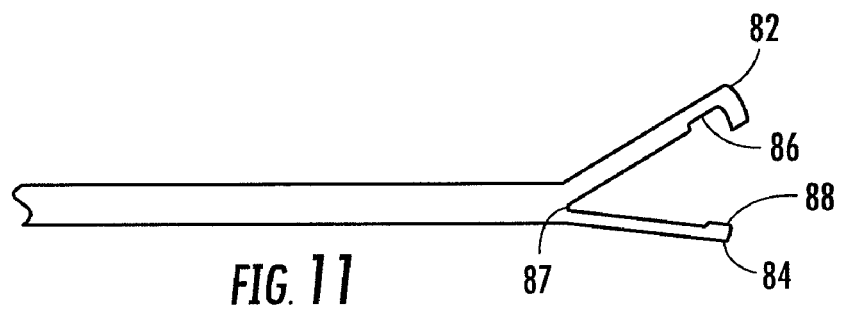
FIG. 11 is an enlarged side view of the embodiment illustrated in FIG. 10 with the end portions spread apart.

FIGS. 10 and 11 illustrate a still further embodiment of the present invention. The end portion 26 of the K-wire or guide wire includes a plurality of deformable ends 82 and 84. The K-wire or guide wire of FIGS. 10 and 11 can be made from a shape memory alloy such as Nitinol. Other shape memory alloys and materials can also be used. The ends 82 and 84 are normally deformed outwardly from the longitudinal axis of the K-wire or guide wire at point 87 as shown in FIG. 11. The deflection of the ends 82 and 84 presents a larger end surface area when the K-wire or guide wire is penetrating a bone. This larger end surface offers more resistance and consequently prevents the K-wire or guide wire from penetrating too far into the bone and perhaps passing into an adjacent bone or outside of the intended bone. The length of the ends 82 and 84 together with the different shape memory alloys determine how quickly the ends 82 and 84 deform outwardly after they enter a bone. The more rapidly they deform, the less they penetrate into a bone. The ends 82 and 84 collapse together, as shown in FIG. 10, when the K-wire or guide wire is withdrawn back through the Jamshidi needle. A groove 86 on end 82 permits projection 88 to fit therein when in the collapsed position.

Figure 12:
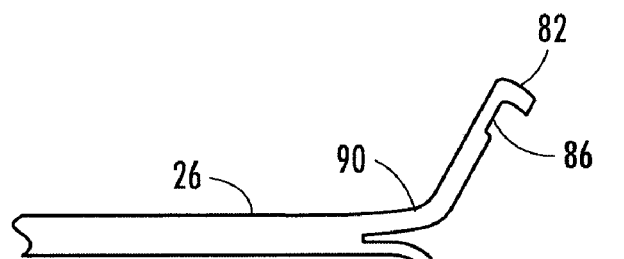
FIG. 12 is an enlarged side view of a still further embodiment of the present invention.
Figure 13:
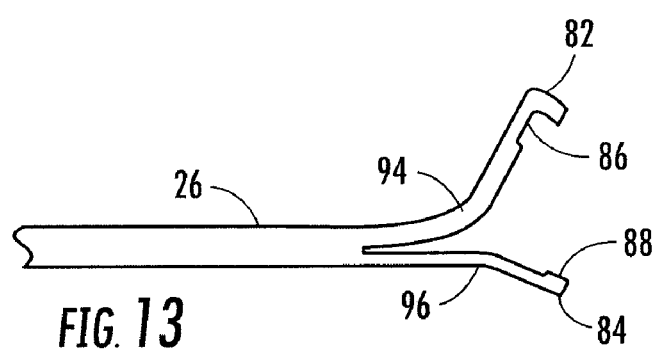
FIG. 13 is an enlarged side view of a still further embodiment of the present invention.

FIGS. 12 and 13 illustrate other embodiments of the present invention. These embodiments are variations of the embodiment illustrated in FIGS. 10 and 11. In FIG. 12 the end 82 of the K-wire or guide wire bends outwardly at 90. Also end 84 bends outwardly at 92. This embodiment permits the ends 82 and 84 to bend outwardly from the longitudinal axis more rapidly than the embodiments of FIGS. 10 and 11. In FIG. 13 the end 82 bends outwardly at 94 and the end 84 bends outwardly at 96. Bends 94 and 96 are closer to the end portions of 82 and 84. Thus, they permit the ends 82 and 84 to bend outwardly from the longitudinal axis more rapidly than the bends 90 and 92 of FIG. 12. The faster the ends move away from the longitudinal axis, the less the K-wire or guide wire penetrates into the bone. Therefore, the embodiment of FIG. 13 would penetrate less into a bone than the embodiment of FIG. 12. Also the embodiment of FIG. 12 would penetrate less into a bone than the embodiment of FIGS. 10 and 11.

Figure 14:
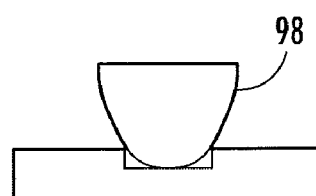
FIG. 14 is a view of the present invention used in a surgical procedure.

The present invention also includes a method of conducting a medical procedure using a K-wire or guide wire, as illustrated in FIG. 14. A surgeon or other medical personnel places a surgical tool end at the surgical site. The initial surgical tool used preferably has a guiding through bore opening at the distal tool end such as that described above for a jamshidi needle 12. A K-wire or guide wire 10 is guided to the site by passing the K-wire or guide wire through the through bore 16 until the operative end 26 extends beyond the open end of the through bore 16. A funnel 98 helps the surgeon place the K-wire or guide wire into the Jamshidi needle. The operative end 26 of the J-wire has at least a portion deformed after its exit from the through bore 16 such that the deformed portion presents a projected area greater than the cross sectional area of the K-wire or guide wire when in the through bore 16 as described above. The deformation can occur automatically as by increasing the temperature of the operative end portion 26 when it includes a memory metal alloy. The deformation may also be induced by relieving stress induced into the operative end portion as when the deformable portion is constructed of a spring material. The deformation may also be induced mechanically by the application of an axially directed force along the K-wire or guide wire 10. After at least a portion of the surgery, the K-wire or guide wire can be removed as described above. The K-wire or guide wire is used to guide surgical tools and/or devices to the surgical site during the surgical procedure. Once the K-wire or guide wire has been inserted into the bone, the jamshidi needle can be withdrawn and a cannulated tap or other instrument can be slid down the K-wire or guide wire and inserted into the bone. When the tap reaches the expanded ends 82, 84 of the K-wire it will stop its forward progress. Thus, this invention avoids the need for fluoroscopy to determine the position of the tap or other instrument in a bone.

It is to be understood that while certain forms of the invention are illustrated, it is not to be limited to the specific forms or arrangements herein described and shown.

It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A guide wire for use in a surgical procedure, the guide wire including: a shank with a distal end portion and a proximal end portion, the distal end portion having a first configuration while inside a constraining through bore of a surgical tool and a second configuration when outside said through bore, said second configuration presenting a larger projected transverse area than the first configuration, said distal end portion being constructed to provide for substantial recoverable deformation from the second configuration back to the first configuration upon axially withdrawing back the guide wire through said through bore of the surgical device; said distal end portion includes a first end portion and a second end portion, wherein each of said first and second end portions are deflected outwardly from a longitudinal axis of the guide wire at a bend point when in the second configuration, wherein said first end portion is longer than said second end portion; said first end portion includes a groove located near free end of said first end portion; said second end portion includes a projection located at free end of said second end portion, wherein said groove permits said projection to fit therein when in said first configuration.

2. The guide wire of claim 1 wherein the distal end portion has a deformable portion made of a memory metal alloy.

3. The guide wire of claim 2 wherein the memory metal alloy includes Nitinol.

4. The guide wire of claim 1 wherein the distal end portion has a deformable portion made of a resiliently deformable spring material.

5. The guide wire of claim 1 wherein the distal end portion has a deformable portion made of a plastically deformable material.

6. The guide wire of claim 1 wherein the second configuration presents a projected transverse area at least about 1.5 times the area of the first configuration.

7. The guide wire of claim 1 wherein said two end portions are deflected outwardly at different locations along said two end portions.

8. A guide wire for use in a surgical procedure, the guide wire including: a shank with a distal end portion and a proximal end portion, the distal end portion being constructed to be changeable from a first configuration to a second configuration at a surgical site, said second configuration presenting a larger projected transverse area than the first configuration to increase resistance to forward axial movement of the guide wire further into a surgical site; said distal end portion includes a first end portion and a second end portion, wherein each of said first and second end portions are deflected outwardly from a longitudinal axis of the guide wire at a bend point when in the second configuration, wherein said first end portion is longer than said second end portion; said first end portion includes a groove located near free end of said first end portion; said second end portion includes a projection located at free end of said second end portion, wherein said groove permits said projection to fit therein when in said first configuration.

9. The guide wire of claim 8 wherein the first end portion has a deformable portion made of a memory metal alloy.

10. The guide wire of claim 9 wherein the memory metal alloy includes Nitinol.

11. The guide wire of claim 8 wherein the first end portion has a deformable portion made of a resiliently deformable spring material.

12. The guide wire of claim 8 wherein the first end portion has a deformable portion made of a plastically deformable material.

13. The guide wire of claim 8 wherein the second configuration presenting a projected transverse area at least about 1.5 times the area of the first configuration.

14. The guide wire of claim 8 wherein said two end portions are deflected outwardly at different locations along said two end portions.

15. A K-wire for use in a surgical procedure, the K-wire including: a shank with a distal end portion and a proximal end portion, the distal end portion having a first configuration while inside a constraining through bore of a surgical tool and a second configuration when outside said through bore, said second configuration presenting a larger projected transverse area than the first configuration, said distal end portion being constructed to provide for substantial recoverable deformation from the second configuration back to the first configuration upon axially withdrawing back the K-wire through said through bore of the surgical device; said distal end portion includes a first end portion and a second end portion, wherein each of said first and second end portions are deflected outwardly from a longitudinal axis of the K-wire at a bend point when in the second configuration, wherein said first end portion is longer than said second end portion; said first end portion includes a groove located near free end of said first end portion; said second end portion includes a projection located at free end of said second end portion, wherein said groove permits said projection to fit therein when in said first configuration.

16. A K-wire for use in a surgical procedure, the K-wire including: a shank with a distal end portion and a proximal end portion, the distal end portion being constructed to be changeable from a first configuration to a second configuration at a surgical site, said second configuration presenting a larger projected transverse area than the first configuration to increase resistance to forward axial movement of the K-wire further into a surgical site; said distal end portion includes a first end portion and a second end portion, wherein each of said first and second end portions are deflected outwardly from a longitudinal axis of the K-wire at a bend point when in the second configuration, wherein said first end portion is longer than said second end portion; said first end portion includes a groove located near free end of said first end portion; said second end portion includes a projection located at free end of said second end portion, wherein said groove permits said projection to fit therein when in said first configuration.

* * * * *